US009345772B1

(12) United States Patent
Parikh et al.

(10) Patent No.: US 9,345,772 B1
(45) Date of Patent: May 24, 2016

(54) LIQUID LEVOTHYROXINE FORMULATIONS

(71) Applicants: Nilesh Parikh, Irvine, CA (US); William Hite, Winchester, CA (US)

(72) Inventors: Nilesh Parikh, Irvine, CA (US); William Hite, Winchester, CA (US)

( * ) Notice: Subject to any disclaimer, the term of this patent is extended or adjusted under 35 U.S.C. 154(b) by 0 days.

(21) Appl. No.: 14/634,452

(22) Filed: Feb. 27, 2015

(51) Int. Cl.
*A61K 31/198* (2006.01)
*A61K 47/10* (2006.01)
*A61K 47/18* (2006.01)

(52) U.S. Cl.
CPC ............. *A61K 47/183* (2013.01); *A61K 31/198* (2013.01); *A61K 47/10* (2013.01)

(58) Field of Classification Search
CPC .... A61K 31/198; A61K 47/10; A61K 47/184
See application file for complete search history.

(56) References Cited

U.S. PATENT DOCUMENTS

| | | | |
|---|---|---|---|
| 5,951,989 A * | 9/1999 | Heymann | 424/401 |
| 6,458,842 B1 | 10/2002 | Dickinson et al. | |
| 7,723,390 B2 | 5/2010 | Garavani et al. | |
| 2014/0073695 A1 * | 3/2014 | Psarrakis et al. | 514/567 |

OTHER PUBLICATIONS

Battaglia et al.; "Solubility and Acid-Base Properties of Ethylenediaminetetraacetic Acid in Aqueous NaCl Solution at $0 \le I \le 6$ mol·kg-1 and T=298.15K"; 2008; J. Chem. Eng. Data; 53: 363-367.*

Fiorucci et al.; "Solubility of Alkali and Alkali Earth Salts of Dihydrogen Ethylenediaminetetraacetate in Aqueous Solutions"; 2002; J. Chem. Eng. Data; 47: 1510-1513.*

* cited by examiner

*Primary Examiner* — Timothy Thomas

(57) ABSTRACT

Embodiments of the present invention provide levothyroxine solutions that consist of from about 0.001% w/v to about 0.01% w/v of a levothyroxine; at least 70% w/w of a glycerol; less than 30% w/w of a water; and from about 0.01% w/w to about 1.5% w/w of an ethylenediaminetetraacetic acid (EDTA). Such levothyroxine solutions are characterized by exhibiting levothyroxine storage stability.

19 Claims, No Drawings

LIQUID LEVOTHYROXINE FORMULATIONS

FIELD OF THE INVENTIONS

The present invention relates to liquid formulations of levothyroxine.

BACKGROUND OF THE INVENTIONS

Thyroid hormones triiodothyronine (T3) and its prohormone thyroxine (T4) are derivatives of the amino acid tyrosine. T4 is produced by the thyroid gland, and metabolized by peripheral tissues to T3. Thyroid hormones are of widespread biological effect on the growth and development and metabolic processes of many different organs and tissues. Deficiencies in T3 and/or T4 are associated with hypothyroidism, the symptoms of which include tiredness, cold sensitivity, weight gain, goiter, decreased muscle tone, myxedema, decreased motor skills, and cretinism.

Levothyroxine sodium is a synthetic form of thyroxine commonly administered to patients suffering from hypothyroidism in thyroid hormone replacement therapy. Levothyroxine is also known as 3,5,3',5'-tetraiodo-L-thyronine, synthetic T4, and L-thyroxine; and the sodium salt of levothyroxine has the chemical formula:

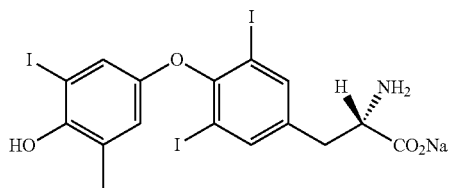

The objective of thyroid hormone replacement therapy is restoration of a euthyroid state. It is, however, well known that levothyroxine has a narrow therapeutic index. The package inserts for several FDA-approved, oral levothyroxine products instruct that, regardless of the indication for use, careful dosage titration is necessary to avoid the consequences of over-treatment or under-treatment. These consequences include, among others, effects on growth and development, cardiovascular function, bone metabolism, reproductive function, cognitive function, emotional state, gastrointestinal function, and glucose and lipid metabolism.

Oral levothyroxine solutions have certain advantages over solid dosage forms. For instance, levothyroxine solutions possess greater potency uniformity than tablets. Tablets often have very low levothyroxine content, which leads to difficulties in achieving drug content uniformity in the manufacturing process. Such that the actual levothyroxine dose that a patient receives with tablet therapy can deviate from label amounts by 20%. Whereas it is much more facile to manufacture homogeneous levothyroxine solutions. In addition, many patients have greater difficulty swallowing tablets than solutions, especially children and the elderly.

Oral levothyroxine solutions also have certain disadvantages compared to solid dosage forms, such as decreased storage stability. But even levothyroxine tablets are known to have storage stability problems. And several regulatory agency approved brands have been subjected to recall due to failure to maintain potency through the expiration date.

The extent of levothyroxine's potency uniformity and storage stability problems is reflected in the United States Food and Drug Administration's (FDA) 1997 action of categorizing all orally administered levothyroxine sodium drug products as new drugs due to significant storage stability and variable potency problems. The FDA required manufacturers of levothyroxine drug products who wished to continue marketing them to submit new drug applications. (See, 62 Fed. Reg. 43535 (Aug. 14, 1997).) In 2012, the United Kingdom's Medicines and Healthcare Products Regulatory Agency issued a Class 2 recall against EVOTROX 25, 50, and 100 microgram levothyroxine solutions because variable stability data failed to provide assurance of product quality.

SUMMARY OF THE INVENTIONS

Embodiments of the invention provide storage-stable, pharmaceutical solutions that contain from about 0.001% w/v to about 0.01% w/v of a levothyroxine; from about 70% w/w to about 99% w/w of a glycerol; from about 1% w/w to about 30% w/w of a water; and from about 0.01% w/w to about 1.5% w/w of an ethylenediaminetetraacetic acid (EDTA). In some embodiments, such solutions, when stored at 70° C. for a 72 hour period, exhibit a decrease of not more than 5% w/w of the levothyroxine. In some embodiments, such solutions, when stored at 40° C. and 75% relative humidity for a six month period, exhibit a decrease of not more than 5% w/w of the levothyroxine. In some embodiments, the EDTA is disodium EDTA. In some embodiments, the solutions comprise from about 0.05% w/w to about 1.0% w/w of the EDTA. In some embodiments, the solutions comprise from about 80% w/w to about 99% w/w of the glycerol. In some embodiments, the solutions comprise from about 85% w/w to about 99% w/w of the glycerol. In some embodiments, the solutions comprise from about 90% w/w to about 99% w/w of the glycerol. In some embodiments, the solutions comprise from about 95% w/w to about 99% w/w of the glycerol. In some embodiments, the solutions have a pH of from between about 5 to about 7.5. In some embodiments, such solutions are free of one or more of added pH adjusting agent, added buffer, and/or added antioxidant.

Embodiments of the invention provide storage-stable, pharmaceutical solutions that contain about 0.002% w/, about 0.004% w/v, about 0.006% w/w, about 0.008% w/w, or about 0.01% w/w of a levothyroxine; from about 80% w/w to about 99% w/w of a glycerol; from about 1% w/w to about 20% w/w of a water; and from about 0.05% w/w to about 1.0% w/w of an EDTA. In some embodiments, such solutions, when stored at 70° C. for a 72 hour period, exhibit a decrease of not more than 5% w/w of the levothyroxine. In some embodiments, such solutions, when stored at 40° C. and 75% relative humidity for a six period, exhibit a decrease of not more than 5% w/w of the levothyroxine. In some embodiments, the levothyroxine is levothyroxine sodium. In some embodiments, the EDTA is disodium EDTA. In some embodiments, the solutions comprise from about 85% w/w to about 99% w/w of the glycerol. In some embodiments, the solutions comprise from about 90% w/w to about 99% w/w of the glycerol. In some embodiments, the solutions comprise from about 95% w/w to about 99% w/w of the glycerol. In some embodiments, the solutions have a pH of from between about 5 to about 7.5. In some embodiments, such solutions are free of one or more of added pH adjusting agent, added buffer, and/or added antioxidant.

DETAILED DESCRIPTION OF THE INVENTIONS

U.S. Pat. No. 6,706,255 ("the '255 patent") discloses that thyroid hormones are known to be unstable in solution and normally exhibit insufficient solubility in water. The '255 patent discloses aqueous, ethanolic solutions of thyroid hormones (preferably levothyroxine) having the following key features. A high ethanol content (40% to 96% by volume), a pH adjusting agent (pH adjusted to pH 9-12), and water (4% to 50% by volume). The '255 patent discloses that its levothyroxine solutions preferably further comprise a sequestrating agent (e.g., sodium ethylenediaminetetraacetic acid (EDTA)), and an antioxidant (e.g., sodium sulfite); and optionally further comprise coloring agents, preservatives, sweetening agents (e.g., glycerin and sodium saccharine), flavoring agents, and thickening agents.

The '255 patent describes its levothyroxine solutions as being stable. Its working examples report stability test results for pH 9.3 adjusted levothyroxine solutions composed of: 0.1% m/v levothyroxine sodium, 0.05% m/v EDTA, 0.05% m/v sodium sulfite, water qs to 100%, and either: (i) 70% v/v ethanol and 0.1% m/v sodium saccharine; or (ii) 40% v/v ethanol and 30% v/v glycerol. The stability tests for these solutions were conducted at monthly intervals for three or six months at 4° C., 25° C., 40° C., and 50° C., in ampoules having air headspace (Examples 1 and 2) or nitrogen headspace (Example 3). At three months, 40° C. and 50° C., and in ampoules having air headspace, solution (ii) exhibited significantly reduced stability compared to solution (i). Stability rescue of solution (ii) at three months, 40° C. and 50° C. required processing the storage ampoule to have a nitrogen headspace (Example 3).

United States Patent Application Publication No. 2014/0073695 ("the '695 publication") discloses levothyroxine sodium solutions and methods for preparing them. The '695 publication reports in its working examples comparative stability test results of levothyroxine solutions conducted for two and six month periods at normal and 40° C. temperatures. The comparator levothyroxine solution in the two and six month stability studies is the 100 μg levothyroxine/5 ml EVOTROX drug product; all samples of which were measured to be pH 5.6 (Table IV) and most samples of which were observed to contain floating particles even prior to conducting pre-stability studies (Table VI). The levothyroxine solution according to the '695 publication in the two and six month stability studies is described as differing from the EVOTROX comparator solution only in its method of preparation. Table I below provides the ingredients and their amounts in the finished formulation of the 100 μg levothyroxine/5 ml solution described by the '695 publication.

TABLE 1

| Ingredient | '695 publication |
| --- | --- |
| Levothyroxine sodium | 100 mcg |
| Glycerol | 2-4 g |
| Citric acid | qs to 5.5 |
| Sodium methylparaben | 0.002-0.009 g |
| Purified water | qs to 5 ml (about 2 g) |
| Sodium hydroxide 1N | qs to 10 |
| Final volume | 5 ml |
| Final pH | 5.5 |

The '695 publication reports in its last Table that the levothyroxine content of the comparator EVOTROX solution was 85.2% and 73.4% of label after two months and 80.8% and 65.8% of label after six months at normal and 40° C. temperatures, respectively. Whereas the levothyroxine content of the solution according to the '695 publication was 106.4% and 104.4% of label after two months and 103.9% and 99.1% of label after six months at normal and 40° C. temperatures, respectively. The '695 publication concludes from the results that the levothyroxine solutions prepared by the methods it describes have higher storage stability.

The '695 publication describes a multistep process for preparing levothyroxine solutions as involving the steps listed in Table 2.

TABLE 2

| | |
| --- | --- |
| a) | providing a salt of levothyroxine, preferably levothyroxine sodium; |
| b) | mixing levothyroxine with an aqueous solvent, preferably a mixture of water and a water-miscible organic solvent; |
| c) | adjusting the pH to at least 8 to yield a basic aqueous solvent (best results obtained by adjusting to pH 9-11, preferably to about pH 10); |
| d) | dissolving the levothyroxine in the basic aqueous solvent to yield a levothyroxine solution; and |
| e) | lowering the pH of the clear levothyroxine solution to between 5-6, preferably to about 5.5. |

The '695 publication additionally describes that its processes for preparing levothyroxine solutions involve not only the above-stated mixing, dissolving, and up and down pH adjusting steps, but can be further multifaceted as follows. The formation, agitation, and controlled and timed heating of a premix composed of a precise ratio of levothyroxine to glycerol, and optionally water. In particular, the '695 publication discloses that a premix can be prepared by dispersing 1 part levothyroxine in 100 parts glycerol by weight; and that water may optionally be added to the premix in an amount below the amount of glycerol. The premix levothyroxine dispersion is agitated and heated to between 40° C. and 50° C. for a period of 15 to 30 minutes, during which part of the levothyroxine dissolves. In a separate vessel, the pH of the remaining water is adjusted to approximately pH 10 with 1N NaOH. This basic solution is added to the partly dissolved levothyroxine dispersion. The final mixture is stirred at 15° C. to 25° C. until a clear solution is obtained. To the clear solution, the sodium methylparaben was added with stirring until a clear solution is obtained. After that, the pH of the solution is adjusted to approximately 5.5 with citric acid, and the volume is adjusted to final by adding a minor amount of water.

The '695 publication teaches that the heating of the dispersion significantly speeded up the dissolving of levothyroxine. And that the dissolving of levothyroxine in basic aqueous solvent is faster compared to dissolving in neutral or acidic water (pH<7).

Embodiments of the present invention provide levothyroxine solutions. In certain embodiments, Levothyroxine solutions of the present invention have the unexpectedly advantageous property of being stable, while also being compositions of reduced ingredient complexity prepared by methods of increased simplicity. In contrast to prior levothyroxine solutions, certain embodiments of levothyroxine solutions according to the present invention are stable without the need for storage under nitrogen, despite: (i) comprising significant amounts of glycerol and no, or low amounts, of ethanol. In addition, some embodiments of levothyroxine solutions according to the present invention are stable without the need for premix formation steps, up and down pH adjustment steps, or timed and controlled heating steps.

In some embodiments, levothyroxine solutions of the present invention comprise levothyroxine dissolved in a glycerol dissolvent system. Glycerol dissolvent systems according to the present invention comprise glycerol and, optionally, one or more glycerol-miscible solvent(s). Glycerol dissolvent systems according to the present invention are operative to solubilize levothyroxine without the need for heating or pH adjusting steps.

In some embodiments, levothyroxine solutions further comprise one or more pharmaceutically acceptable excipients(s) including, without limitation, chelating agents and antioxidants.

In some embodiments, levothyroxine solutions are pH adjusted, in a single direction, to about pH 6, about pH 6.5, about pH 7, about pH 7.5, about pH 8, about pH 8.5, about pH 9, about pH 9.5, about pH 10, about pH 10.5, about pH 11, about pH 11.5, or ranges therebetween.

Glycerol.

Levothyroxine solutions according to the invention may contain, by weight of the finished solution, one or more glycerol-miscible solvent(s) in aggregate amounts of about 70%, about 75%, about 80%, about 85%, about 90%, about 95%, about 97%, about 99%, about 100% or ranges therebetween.

Glycerol-Miscible Solvents.

Glycerol miscible solvents useful in the present in invention include water and ethanol. Levothyroxine solutions according to the invention may contain, by weight of the finished solution, one or more glycerol-miscible solvent(s) in aggregate amounts of about 30%, about 25%, about 20%, about 15%, about 10%, about 5%, about 2.5%, about 1%, about 0.5% or ranges therebetween.

Chelators.

Chelators useful in the present invention include, without limitation, deferoxamine (DEF), EDTA, salts thereof, derivatives thereof, and combinations thereof. Levothyroxine solutions according to the invention may contain, by weight of the finished solution, one or more chelator(s) in aggregate amounts of about 0.001%, about 0.005%, about 0.01%, about 0.05%, about 0.1%, about 0.5%, about 1%, about 2%, or ranges therebetween.

Antioxidants.

Antioxidants useful in the present invention include, without limitation, propyl gallate, butylated hydroxyanisole (BHA), butylated hydroxytoluene (BHT), vitamin E, β-carotene, thioglycolic acid, thioglycerol, dithioerythreitol, acetyl cysteine, and ascorbic acid. Levothyroxine solutions according to the invention may contain, by weight of the finished solution, one or more antioxidant(s) in aggregate amounts of about 0.001%, about 0.005%, about 0.01%, about 0.05%, about 0.1%, about 0.5%, about 1%, about 2%, or ranges therebetween.

Certain of the following examples illustrate specific embodiments of the invention and are not meant to limit the scope of the invention.

Example 1

Levothyroxine sodium Test solutions were made according to the processes described by the '695 publication, with the composition set forth in Example 2.

Example 2

The Test solutions according to the '695 publication had the following composition

TABLE 3

| Test Solution | |
| --- | --- |
| Ingredient | Amount |
| Levothyroxine sodium | 100.0 mcg |
| Glycerol | 3780.0 mg |
| Methylparaben sodium | 9.0 mg |
| Sodium hydroxide | q.s. to pH 10 |
| Citric acid | q.s. to pH 5.5 |
| Water | 1991.0 mg |
| Final volume | 5.0 ml |

Example 3

Levothyroxine sodium solutions according the present invention, with compositions set forth in Table 4, are made by the process set forth in Example 4.

TABLE 4

| Levothyroxine Sodium Solutions | |
| --- | --- |
| Ingredient | Amount (w/w) |
| Levothyroxine | 0.001%-0.01% |
| Glycerol[1] | 75%-100% |
| Glycerol-miscible solvent[1] | 0.000%-30.00% |
| Chelator | 0%-1.5% |
| Antioxidant | 0%-0.01% |

[1]Glycerol dissolvent system

Example 4

Levothyroxine sodium solutions according to the present invention can be made by forming a glycerol dissolvent system of glycerol or glycerol and one or more glycerol-miscible solvent(s), in amounts according to Table 4. And dissolving, in the glycerol dissolvent system, levothyroxine sodium and, optionally, one or more chelator(s) and/or antioxidant(s), in amounts according to Table 4. None of the levothyroxine (e.g., levothyroxine sodium), chelator(s), or antioxidant(s) need be added to the glycerol dissolvent system in any particular order, sequence, or combination. And in embodiments in which the glycerol dissolvent system includes a glycerol-miscible solvent, each of the levothyroxine, chelator(s), and antioxidant(s) may be added to: i. either the glycerol or the glycerol-miscible solvent prior to their combination to form the glycerol dissolvent system, or ii. the formed glycerol dissolvent system. Each of the levothyroxine sodium, chelator(s), and antioxidant(s) may be added to aforementioned i. and ii. in solid form (e.g., particles or grains or powders or dusts or crystals), solution form, or suspension form.

Suitable techniques for dissolving levothyroxine sodium, chelator(s), and antioxidant(s) in glycerol, glycerol-miscible solvents, and glycerol dissolvent systems include mixing by homogenization, stirring, shaking, swirling, and the like. Mixing and dissolving steps performed in forming levothyroxine sodium solutions of the invention may conveniently be conducted at room temperature or at elevated temperatures such as 30° C. to 50° C.

Example 5

Levothyroxine sodium solutions according the present invention with the compositions set forth in Table 5 were made as described in Example 6.

TABLE 5

| Ingredient name | Solution name | | | | |
|---|---|---|---|---|---|
| | Solution 1 | Solution 2 | Solution 3 | Solution 4 | Solution 5 |
| Levothyroxine sodium | 0.0017% w/w | 0.0017% w/w | 0.002% w/v | 0.0017% w/w | 0.01% w/w |
| Glycerol | 79.42% w/w | 75.89% w/w | 72.31% w/w | 68.65% w/w | 99.91% w/w |
| Water | 20.56% w/w | 24.09% w/w | 27.68% w/w | 31.33% w/w | None added |
| EDTA | 0.067% w/w | 0.067% w/w | 0.067% w/w | 0.068% w/w | 0.08% w/w |

Example 6

Solution 1.

Solution 1 was made heating 95 g glycerol to 45° C. to while stirring. Separately, 0.08 g EDTA was added to 5 gm of water, which was then added to the 45° C. glycerol, and then stirred for 15 min. Next, 0.002 g levothyroxine sodium was dissolved in the glycerol+water+EDTA solution, and stirred at 45° C. for 45 minutes. Finally, the volume of the glycerol+water+EDTA was adjusted to 100 ml with water. The resulting levothyroxine Solution 1 was filled into an amber type III glass bottle and capped.

Solution 2.

Solution 2 was made heating 90 g glycerol to 45° C. to while stirring. Separately, 0.08 g EDTA was added to 10 gm of water, which was added to the 45° C. glycerol, and then stirred for 15 min. Next, 0.002 g levothyroxine sodium was dissolved in the glycerol+water+EDTA solution, and stirred at 45° C. for 45 minutes. Finally, the volume of the glycerol+water+EDTA was adjusted to 100 ml with water. The resulting levothyroxine Solution 2 was filled into an amber type III glass bottle and capped.

Solution 3.

Solution 3 was made heating 85 g glycerol to 45° C. to while stirring. Separately, 0.08 g EDTA was added to 15 gm of water, which was added to the 45° C. glycerol, and then stirred for 15 min. Next, 0.002 g levothyroxine sodium was dissolved in the glycerol+water+EDTA solution, and stirred at 45° C. for 45 minutes. Finally, the volume of the glycerol+water+EDTA was adjusted to 100 ml with water. The resulting levothyroxine Solution 3 was filled into an amber type III glass bottle and capped.

Solution 4.

Solution 4 was made heating 80 g glycerol to 45° C. to while stirring. Separately, 0.08 g EDTA was added to 20 gm of water, which was added to the 45° C. glycerol, and then stirred for 15 min. Next, 0.002 g levothyroxine sodium was dissolved in the glycerol+water+EDTA solution, and stirred at 45° C. for 45 minutes. Finally, the volume of the glycerol+water+EDTA was adjusted to 100 ml with water. The resulting levothyroxine Solution 4 was filled into an amber type III glass bottle and capped.

Solution 5.

Solution 5 was made heating 99.91 g glycerol to 45° C. to while stirring, to which 0.08 g EDTA and 0.01 g levothyroxine sodium were added, and then stirred at 45° C. for 45 minutes. Finally, the volume of the glycerol+water+EDTA was adjusted to 100 ml with water. The resulting levothyroxine Solution 4 was filled into an amber type III glass bottle and capped.

The pH of Solutions 1-5 fell in a range of from pH 5.4 to 6.5.

Example 7

Stability studies are conducted on samples of Test solutions and levothyroxine sodium solutions according to the present invention stored in capped, amber type III glass bottles at 70° C. for three days. The equipment used in conducting stability studies is a high performance liquid chromatography (HPLC) system with BEH C18, 1.7 μm sorbent, 2.1×50 mm columns and Empower software. Reagents, gradients, and reference solutions employed in the HPLC stability studies are set forth in Tables 6, 7, and 8.

TABLE 6

HPLC Reagents

Levothyroxine Sodium (standard substance)
Diiodo(3,5)-L-thyronine (standard substance)
Liothyronine Sodium (standard substance)
Levothyroxine for SST (standard substance)
Levothyroxine for SST 2 (standard substance 2)
Methanol
Acetonitrile
Phosphoric acid, 85%
Sodium hydroxide, 1 mol/l
Water
Mobile phase A is 1.0 ml phosphoric acid diluted in water to obtain 1000 ml.
Mobile phase B is 1.0 ml phosphoric acid diluted in acetonitrile to obtain 1000 ml.
Weak needle wash mix is 100 ml acetonitrile with 900 ml water (1000 μl).
Strong needle wash is methanol (1000 μl).
Solvent is methanol.
Column temperature 53.5° C. (±1.5° C. see system suitability).
Sample temperature 20° C.
Detection Spectrophotometric at 225 nm.
Detector settings Sampling Rate: 20 pt/s.
Transmission Ultraviolet (TUV) Filter Time Constant: 0.2 (slow).
Photo Diode Array (PDA) Filter Time Constant: 0.2.
Total registration time: 19 min.
Flow 0.7 ml/min.

TABLE 7

HPLC Gradient Table

| Time (Minutes) | Mobil Phase A (%) | Mobil Phase B (%) |
|---|---|---|
| 0 (Start) | 83 | 17 |
| 3.1 | 78 | 22 |
| 15.5 | 1 | 99 |
| 17 | 1 | 99 |
| 17.2 | 83 | 17 |
| 19 | 83 | 17 |

TABLE 8

HPLC Suitability and Reference Solutions

| System suitability solution 1 | Add 20 mg levothyroxine SST to 5 ml solvent in a 25 ml volumetric flask and allow to stand for 20 minutes. 0.5 ml sodium hydroxide is added and fill up to volume with solvent. |

TABLE 8-continued

HPLC Suitability and Reference Solutions

| | |
|---|---|
| System suitability solution 2 | Add 20 mg levothyroxine SST2 to 5 ml solvent in a 25 ml volumetric flask and allow to stand for 20 minutes. 0.5 ml sodium hydroxide is added and a fill up to volume with solvent. |
| Test solution | Add 80 mg stability test solution to 20 ml solvent in a 100 ml volumetric flask and allow to stand for 20 minutes. Add 2.0 ml sodium hydroxide and fill up to volume with solvent (corresponding to a 0.8 mg/ml or 100% solution). |
| Reference solution 1 | Add 80 mg levothyroxine sodium standard substance to 20 ml solvent in a 100 ml volumetric flask and allow to stand for 20 minutes. Add 2.0 ml sodium hydroxide and fill up to volume with solvent (corresponding to a 0.8 mg/ml or 100% levothyroxine sodium solution). |
| Reference solution 2 | Add 20 mg diiodo(3,5)-L-thyronine standard substance to 5 ml solvent, followed by 0.5 ml sodium hydroxide to dissolve the substance in a 25 ml volumetric flask and fill up to volume with solvent (corresponding to a 0.8 mg/ml Diiodo(3,5)-L-thyronine solution). |
| Reference solution 3 | Add 20 mg liothyronine standard substance to 5 ml solvent, followed by 0.5 ml sodium hydroxide to dissolve the substance in a 25 ml volumetric flask and fill up to volume with solvent (corresponding to a 0.8 mg/ml liothyronine solution). |
| Reference solution 4 | Dilute 2.0 ml of reference solution 1 and 2.0 ml of reference solution 2 with solvent to obtain 50 ml (corresponding to a 0.032 mg/l levothyroxine and 0.032 mg/l diiodo(3,5)-L-thyronine solution). |
| Reference solution 5 | Dilute 2.5 ml of reference solution 4 and 1 ml reference solution 3 with solvent to obtain 100 ml (corresponding to 0.1% Levothyroxine sodium, 0.1% diiodo(3,5)-L-thyronine and 1.0% liothyronine sodium). |
| Blank solution | Mix 0.5 ml sodium hydroxide with solvent to obtain 25 ml |
| Injection mode | Partial Loop With Needle Overfill. |
| Solution injection volumes | 1.0 μl test solution<br>1.0 μl reference solution 1 (for assay)<br>1.0 μl reference solution 5 (for related compounds)<br>1.0 μl system suitability solution 1<br>1.0 μl system suitability solution 2<br>1.0 μl blank solution |

The chromatographic parameters R and T are calculated according to USP using the following equations:

$$R = \frac{2 * (t_{R2} \cdot t_{R1})}{W_2 + W_1}$$

$$T = \frac{W_{0.05}}{2f}$$

In the R and T equations: $t_{R2}$=retention time of the later eluting peak; $t_{R1}$=retention time of the earlier eluting peak; $W_1$=peak width of the earlier eluting peak at its base, obtained by extrapolating the tangents to the baseline; $W_2$=peak width of the later eluting peak at its base, obtained by extrapolating the tangents to the baseline; $W_{0.05}$=peak width at 5% of the peak height; and 2f=distance from the leading edge of the peak to $t_R$ at 5% of the peak height.

Identity. The retention time of the principal peak in the chromatogram of the test solution and that of the levothyroxine peak in system suitability solution must be concordant (identity).

Related Compounds. Peaks corresponding to those in the chromatogram of the blank solution are not taken into account. Diiodo(3,5)-L-thyronine and liothyronine are calculated against their individual standard in reference solution 5. All other known and unknown related compounds are calculated against levothyroxine sodium in reference solution 5 according to the following equation:

$$\% (w/w) \text{ of impurity} = \frac{\text{Area}_i \cdot W_{ref} \cdot P}{\text{Area}_{ref} \cdot W_i \cdot (100 - WC\%)/100 \cdot C_i \cdot 1000}$$

In the % (w/w) of impurity equation: $\text{Area}_i$=area of the impurity peak in the test solution; $W_{ref}$=weight of the respective reference substance in reference solution 1; P=purity "as is" of the reference substance in %; $\text{Area}_{ref}$=area of the respective reference peak in reference solution 5; $W_i$=weight of the sample in mg; WC %=water content of the sample in %; 1000=Factor (denominator) corresponding to the dilution of reference solution 5; and $C_i$=conversion factor (numerator) to calculate the amount of a given test sample: i.e., 1.0000 for Levothyroxine sodium; 0.9732 for Levothyroxine di-sodium; and 0.8654 for Levothyroxine bis(butylammonium). Limits of quantitation are 0.01% for 3,5-Diiodo-L-thyronine, 0.01% for liothyronine, and 0.01%, for levothyroxine and unknown compounds.

Levothyroxine content is calculated against Levothyroxine Sodium in reference solution 1 according to the following equation:

$$\% (w/w) \text{ of levothyroxine} = \frac{\text{Area}_i \cdot W_{ref} \cdot P}{\text{Area}_{ref} \cdot W_i \cdot (100 - WC\%)/100}$$

In the % (w/w) of levothyroxine equation: $\text{Area}_i$=area of the levothyroxine peak in the test solution; Wref=weight of the reference substance in reference solution 1; P=purity "as is" of the reference substance in %; $\text{Area}_{ref}$=area of the reference peak in reference solution 1; Wi=weight of the sample in mg; WC %=water content of the sample in %. If more than one determination is carried out, the final result is calculated as the mean value of the single values according to:

$$\text{Final result} = \frac{1}{N} \sum_{i=1}^{N} r_i$$

In the final result equation: N=# of determinations and $r_i$=result of determination number i.

Example 8

Stability studies as described in Example 7 were conducted on samples of Test solution described in Examples 1-2 and levothyroxine sodium solutions 1-5 according to the present invention described in Examples 5-6. Levothyroxine sodium solutions according to the present invention possess surprisingly advantageous stability properties, as described in Table 9.

TABLE 9

| Solution name | Time | T3 | Assay | Assay delta |
|---|---|---|---|---|
| Test solution* | Initial | 0.02 | 90.2 | 8.7 |
| | 3 days 70° C. | 3.7 | 81.5 | |

TABLE 9-continued

| Solution name | Time | T3 | Assay | Assay delta |
|---|---|---|---|---|
| Solution 1 | Initial | BQD** | 105.2 | 2.4 |
| | 3 days 70° C. | 1.65 | 102.8 | |
| Solution 2 | Initial | BQD | 103.4 | 4.2 |
| | 3 days 70° C. | 1.93 | 99.2 | |
| Solution 3 | Initial | BQD | 105.5 | 4.8 |
| | 3 days 70° C. | 2.84 | 100.7 | |
| Solution 4 | Initial | BQD | 98.2 | 4 |
| | 3 days 70° C. | 3.36 | 94.2 | |
| Solution 5 | Initial | ND*** | 98.6 | 7.2 |
| | 3 days 70° C. | ND | 91.4 | |

*The data of the Test solutions in this Table 9 is the average of three Test solutions.
**BQD = below quantitative detection
***ND = none detected Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

We claim:

1. A pharmaceutical solution comprising:
from 0.001% w/v to 0.01% w/v of a levothyroxine;
from 75% w/w to 95% of glycerol;
from 0.01% w/w to 1.5% w/w of an ethylenediaminetetraacetic acid (EDTA); and
an amount of water sufficient to adjust the pharmaceutical solution to 100% w/w, and
wherein the solution is storage stable.

2. The pharmaceutical solution of claim 1, wherein the levothyroxine is levothyroxine sodium.

3. The pharmaceutical solution of claim 2, wherein the EDTA is disodium EDTA.

4. The pharmaceutical solution of claim 3, wherein the solution comprises from 0.05% w/w to 1.0% w/w of the disodium EDTA.

5. The pharmaceutical solution of claim 4, wherein the solution comprises from 80% w/w to 95% w/w of the glycerol.

6. The pharmaceutical solution of claim 5, wherein the solution comprises from 85% w/w of 95% w/w glycerol.

7. The pharmaceutical solution of claim 6, wherein the solution comprises from 90% w/w to 95% w/w glycerol.

8. A pharmaceutical solution comprising:
0.002% w/v, 0.004% w/v, 0.006% w/v, 0.008% w/v, or 0.01% w/v of a levothyroxine;
from 75% w/w to 95% w/w glycerol;
from 0.05% w/w to 1.5% w/w of an EDTA; and
an amount of water sufficient to adjust the pharmaceutical solution to 100% w/w, and
wherein the solution is storage stable.

9. The pharmaceutical solution of claim 8, wherein the levothyroxine is levothyroxine sodium.

10. The pharmaceutical solution of claim 9, wherein the EDTA is disodium EDTA.

11. The pharmaceutical solution of claim 10, wherein the solution comprises from 80% w/w to 95% w/w glycerol.

12. The pharmaceutical solution of claim 11, wherein the solution comprises from 85% w/w to 95% w/w glycerol.

13. The pharmaceutical solution of claim 12, wherein the solution comprises from 90% w/w to 95% w/w glycerol.

14. A pharmaceutical solution comprising:
0.002% w/v or 0.004% w/v of a levothyroxine;
from 75% w/w to 95% w/w glycerol;
from 0.05% w/w to 1.0% w/w of an EDTA,
an amount of water sufficient to adjust the pharmaceutical solution to 100% w/w, and
wherein the solution is storage stable.

15. The pharmaceutical solution of claim 14, wherein the solution comprises from 80% w/w to 95% w/w glycerol.

16. The pharmaceutical solution of claim 15, wherein the solution comprises from 85% w/w to 95% w/w glycerol.

17. The pharmaceutical solution of claim 14, wherein the solution comprises from 90% w/w to 95% w/w glycerol.

18. A pharmaceutical solution comprising:
from 0.002% w/v to 0.006% w/w of a levothyroxine sodium;
from 90% w/w to 95% w/w glycerol;
an amount of water sufficient to adjust the pharmaceutical solution to 100% w/w; and
0.08% w/w of an EDTA, and
wherein the solution is storage stable.

19. The pharmaceutical solution of claim 18, wherein the levothyroxine is levothyroxine sodium, and wherein the EDTA is disodium EDTA.

* * * * *